United States Patent
Juloski et al.

(10) Patent No.: US 8,944,999 B2
(45) Date of Patent: Feb. 3, 2015

(54) COIL SYSTEM FOR THE CONTACTLESS MAGNETIC NAVIGATION OF A MAGNETIC BODY IN A WORK SPACE

(75) Inventors: Aleksandar Juloski, Nuremberg (DE); Johannes Reinschke, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 655 days.

(21) Appl. No.: 12/998,225

(22) PCT Filed: Aug. 26, 2009

(86) PCT No.: PCT/EP2009/060957
§ 371 (c)(1),
(2), (4) Date: Mar. 28, 2011

(87) PCT Pub. No.: WO2010/034582
PCT Pub. Date: Apr. 1, 2010

(65) Prior Publication Data
US 2011/0181995 A1  Jul. 28, 2011

(30) Foreign Application Priority Data

Sep. 26, 2008  (DE) .......................... 10 2008 049 198

(51) Int. Cl.
*A61B 1/00* (2006.01)
*H01F 7/18* (2006.01)
*A61B 19/00* (2006.01)

(52) U.S. Cl.
CPC ......... *A61B 19/22* (2013.01); *A61B 2019/2253* (2013.01)
USPC ........... 600/117; 600/101; 600/118; 361/143; 361/144

(58) Field of Classification Search
USPC ........................... 600/101, 118, 117; 361/143
See application file for complete search history.

(56) References Cited

U.S. PATENT DOCUMENTS

| 4,585,282 A | 4/1986 | Bosley |
| 6,230,038 B1 | 5/2001 | von Gutfeld et al. |

(Continued)

FOREIGN PATENT DOCUMENTS

| CN | 101220894 A | 7/2008 |
| DE | 103 41 092 | 4/2005 |

(Continued)

OTHER PUBLICATIONS

M V Berry et al., "Of Flying Frogs and Levitrons," European Journal of Physics, vol. 18, No. 4, Jul. 1, 1997, pp. 307-313.

(Continued)

*Primary Examiner* — Rexford Barnie
*Assistant Examiner* — Angela Brooks
(74) *Attorney, Agent, or Firm* — Staas & Halsey LLP

(57) ABSTRACT

A coil system for the contactless magnetic navigation of a magnetic body in a work space, has a plurality of coils and a current controller for controlling the respective currents in the plurality of coils. In order to navigate the magnetic body to a variably predeterminable position in the work space, the current controller is designed such that the currents in the plurality of coils are such that the magnetic forces generated by the currents and acting upon the magnetic body at multiple positions at the edge of a convex environment around the predetermined position are directed into the environment. The coil system has the advantage that a movement of the magnetic body toward a spatial position is achieved without any mechanical movement of the coil system and without a positioning system for determining the position of the magnetic body. The coil system is utilized particularly in a medical device, wherein a magnetic body in the form of a probe is moved in the body of a patient. In this way, fast navigation of the probe in the patient's body can be achieved without mechanical movements of the patient table or of the coil system.

20 Claims, 2 Drawing Sheets

(56) References Cited

U.S. PATENT DOCUMENTS

| | | | |
|---|---|---|---|
| 7,122,001 B2* | 10/2006 | Uchiyama et al. | 600/103 |
| 7,348,691 B2 | 3/2008 | Davis et al. | |
| 7,505,243 B2 | 3/2009 | Davis et al. | |
| 7,654,985 B2* | 2/2010 | Dinsmoor et al. | 604/174 |
| 7,663,458 B2 | 2/2010 | Reinschke et al. | |
| 8,241,206 B2* | 8/2012 | Kawano | 600/117 |
| 8,316,861 B2* | 11/2012 | Brewer et al. | 128/899 |
| 8,317,681 B1* | 11/2012 | Gazdzinski | 600/118 |
| 2003/0181788 A1* | 9/2003 | Yokoi et al. | 600/160 |
| 2004/0030324 A1 | 2/2004 | Creighton, IV et al. | |
| 2004/0050394 A1 | 3/2004 | Jin | |
| 2005/0062562 A1 | 3/2005 | Ries | |
| 2005/0065407 A1* | 3/2005 | Nakamura et al. | 600/160 |
| 2005/0093544 A1 | 5/2005 | Ries | |
| 2005/0222537 A1* | 10/2005 | Dinsmoor et al. | 604/174 |
| 2007/0016006 A1 | 1/2007 | Shachar | |
| 2007/0221233 A1* | 9/2007 | Kawano et al. | 128/899 |
| 2007/0244388 A1* | 10/2007 | Sato et al. | 600/424 |
| 2007/0270628 A1 | 11/2007 | Kawano et al. | |
| 2007/0290814 A1* | 12/2007 | Yoshida | 340/10.34 |
| 2008/0262292 A1* | 10/2008 | Abraham-Fuchs et al. | 600/101 |
| 2008/0300459 A1* | 12/2008 | Kimura et al. | 600/118 |
| 2008/0306340 A1 | 12/2008 | Uchiyama et al. | |
| 2008/0312501 A1* | 12/2008 | Hasegawa et al. | 600/117 |
| 2010/0179782 A1* | 7/2010 | Kimura et al. | 702/94 |
| 2010/0234685 A1* | 9/2010 | Juloski et al. | 600/117 |
| 2011/0313266 A1* | 12/2011 | Fortsch et al. | 600/345 |

FOREIGN PATENT DOCUMENTS

| | | |
|---|---|---|
| JP | 2005-58430 | 3/2005 |
| JP | 2005-81147 | 3/2005 |
| WO | 2004/030198 | 4/2004 |
| WO | 2006/014011 | 2/2006 |
| WO | 2006/092421 | 9/2006 |
| WO | 2006/128160 | 11/2006 |
| WO | 2007/077896 A1 | 7/2007 |
| WO | 2007/077922 | 7/2007 |

OTHER PUBLICATIONS

PCT/EP2009/060957, Aug. 26, 2009, Aleksandar Juloski et al., Siemens AG.

DE 10 2008 049 198.5, Sep. 26, 2009, Aleksandar Juloski et al., Siemens AG.

International Search Report for PCT/EP2009/060957, mailed on Dec. 28, 2009.

German Office Action for Priority Application No. DE 10 2008 049 198.5, issued Jun. 9, 2009.

Chinese Office Action issue May 16, 2013 in corresponding Chinese Application No. 200980147207.9.

Office Action issued by the State Intellectual Property Office of the P.R. China in Mar. 13, 2014 in the corresponding Chinese patent application No. 200980147207.9.

Office Action issued by the State Intellectual Property Office of the P.R. China on Oct. 17, 2014 in the corresponding Chinese patent application No. 200980147207.9.

* cited by examiner

COIL SYSTEM FOR THE CONTACTLESS MAGNETIC NAVIGATION OF A MAGNETIC BODY IN A WORK SPACE

CROSS REFERENCE TO RELATED APPLICATIONS

This application is based on and hereby claims priority to International Application No. PCT/EP2009/060957 filed on Aug. 26, 2009 and German Application No. 10 2008 049 198.5 filed on Sep. 26, 2008, the contents of which are hereby incorporated by reference.

BACKGROUND

The invention relates to a coil system and to a method for the contactless navigation of a magnetic body in a work space.

Coil systems for the contactless magnetic navigation of a magnetic body use a plurality of coils to produce a magnetic field which interacts with the magnetic body, whereby magnetic forces and torques are generated which cause the movement of the magnetic body. The magnetic force and the magnetic torque, which act on the magnetic body, can be suitably adjusted by way of the corresponding currents into the individual coils of the coil system.

Coil systems of the above type are used in particular in the medical field. Here a patient is examined in the work space of the coil system using the magnetic body. The work space is accessible from the outside and in this space the magnetic forces of the coil system have an adequate effect on the magnetic body. To carry out the examination the magnetic body, which is located in the patient, and the part of the patient's body to be examined are introduced into the work space of the coil system. The magnetic body is a probe with which measurements on—in particular images of—a patient's internal organs can be taken.

A coil system with magnetic probe is used, for example, in gastroenterology, in particular gastroscopy, see WO 2007/077922 A1. During the endoscopic examination the patient's stomach is partially filled with water and the patient swallows an appropriate probe which contains a permanent magnet and a camera.

Here the patient's stomach is located in the work space of the coil system or is introduced into the work space after the probe has been swallowed. By using the magnetic forces and torques generated by the coil system the probe is moved in such a way that images of the areas of the patient's gastric mucosa to be examined are produced. It is necessary in this connection for it to be possible by way of suitably energizing the coils to generate an inhomogeneous magnetic field such that the probe is appropriately positioned and is kept in this position by the interaction of this magnetic field with the permanent magnet in the probe.

Various approaches are known from the related art for appropriately positioning a magnetic body relative to a coil system. A coil system is known from WO 2006/014011 A1 in which, during the examination, the patient to be examined is moved in relation to the coil system. The coil system is constructed in such a way that a single spatial point exists which is fixed in relation to the coil system. If no external forces act on the magnetic body the body moves toward this spatial point as a result of the magnetic forces and torques exerted. When the magnetic body has reached this spatial point it remains there provided no forces are exerted from the outside. It has proven disadvantageous in this connection that either the coil system or the patient or both have to be mechanically moved in order to move the magnetic body. This is a problem in particular in applications in which rapid movement of the magnetic body toward a predetermined position is required.

Systems are also known from the related art in which the coil system is replaced by one or more permanent magnet(s) in order to move a magnetic body, see for example U.S. Pat. No. 7,019,610 B2. The movement toward a predetermined position is achieved by a mechanical movement of the patient or the permanent magnet or patient and permanent magnet in this system as well.

Coil systems are also known from the related art in which, without mechanical movement, by appropriate adjustment of the magnetic fields and field gradients, to the position of the magnetic body a movement of the magnetic body is achieved that is caused merely by the currents in the coil system (see for example WO 2006/092421 A1). However, it is necessary here for the position and orientation of the magnetic body to be known, and this in turn means that the position of the magnetic body also has to be measured.

SUMMARY

One possible object is to avoid the drawbacks of the related art described above and to create a coil system and a method with which a magnetic body can easily be contactlessly navigated.

The inventors propose a coil system having a plurality of coils and a current controller for controlling the respective currents in the plurality of coils. In order to navigate a magnetic body to a variably predeterminable position in the work space of the coil system, the current controller is designed such that the currents in the plurality of coils are adjusted in such a way that the magnetic forces generated by the currents and acting upon the magnetic body at multiple positions at the edge of a convex environment around the predeterminable position are directed into the environment. "Variably predeterminable" is here taken to mean that the position in the work space is not fixed, but may be variably adjusted by the current controller. The magnetic body is designed in particular such that it has a predetermined magnetic dipole moment in a specified direction.

Such control of the currents ensures that, independently of the current position of the magnetic body in the work space, a movement of the body toward the predeterminable position is always ensured. The predeterminable position can be adjusted for example by the user by way of a user interface. A convex environment is taken to mean an environment which does not have any regions that are inwardly curved. The convex environment must be located in the work space of the coil system in this case. The environment is preferably located in the vicinity of the predeterminable position. Vicinity denotes in particular that the maximum spacing of the edge of the environment is 10% or less from the largest extent of the coil system. For medical applications environments whose edge has a maximal spacing between 0.005 m and 0.1 m, preferably of 0.01 m, from the predeterminable position in particular have proven to be practicable.

The coil system has the advantage that a magnetic field maximum ("peak") can be created with substantially forces directed toward the predeterminable position merely by an appropriate current controller. It is not necessary for the coil system to be mechanically moved here, and the current position of the magnetic body in the work space is known. Determination of this current position may therefore be omitted.

In a preferred embodiment the environment around the predeterminable position is a polygon and/or a polyhedron, for example a triangle, square or other quadrilateral. A polygon is particularly expedient if the movement of the magnetic body has less than three translational degrees of freedom. The plurality of positions, on which the magnetic forces act at the edge of the environment for a magnetic body positioned there, are preferably located at one or more of the corner(s) of the polygon and/or polyhedron, in particular at all corners of the polygon and/or polyhedron.

In a preferred embodiment of the coil system the current controller is designed in such a way that the currents are calculated for the predeterminable position by the current controller during operation of the coil system. The currents suitable for a certain position are therefore determined in real time. It is likewise possible for the currents to be adjusted for a large number of predeterminable positions to be stored in a memory of the current controller. If a spatial position toward which the magnetic body should move, is fixed for example by way of a user interface, the corresponding currents to be adjusted are then read out of this memory.

In a particularly preferred embodiment the currents to be adjusted in order to navigate the magnetic body to the predeterminable position represent the solution to an optimization problem with the boundary condition that the magnetic forces generated by the currents and acting upon the magnetic body at multiple positions at the edge of the convex environment around the predeterminable position are directed into the environment. In a preferred embodiment the optimization problem is a linear program and/or a quadratic program which can be reliably solved in a short calculating time using known standard optimization methods.

In a preferred embodiment the optimization problem is the minimization of the value, or the 2-norm (i.e. the Euclidean norm) of the vector of the currents in the plurality of coils while taking account of the additional boundary condition that the magnetic forces generated by the currents and acting upon the magnetic body at multiple positions at the edge of the convex environment around the predeterminable position exceed a predetermined value respectively.

In a further embodiment of the coil system the currents are weighted differently when solving the optimization problem. Instead of the 2-norm of the vector of the coil currents, the 2-norm of a weighted vector of the coil currents is minimized for example, with each individual coil current being weighted with the square root of the ohmic resistance of the coils. The ohmic total power loss is minimized in the plurality of coils as a result.

Alternatively or additionally the optimization problem can also be defined in such a way that the magnetic forces generated by the currents and acting upon the magnetic body at multiple positions at the edge of the convex environment around the predeterminable position are maximized. It is taken into account as an additional boundary condition that the value of currents of the plurality of coils is below a respective maximum value.

In a particularly preferred embodiment it is taken into account when solving the optimization problem described above as an additional boundary condition that the magnetic field generated by the currents at the predeterminable position is substantially directed in a predetermined direction and has a value which exceeds a predetermined value. This ensures that the magnetic body also has a specified orientation toward the predeterminable position.

In a further embodiment of the coil system the current controller takes account of a movement of the magnetic body with two translational degrees of freedom or less.

The coil system is preferably used in a medical device which is designed in such a way that a patient can be positioned in the coil system and a magnetic body in the form of a probe for examining the organs in the patient can be navigated to predeterminable positions inside the patient's body by the current controller.

The inventors also propose a method for the contactless magnetic navigation of a magnetic body in a work space using an coil system. In order to navigate the magnetic body to a predeterminable position in the work space, the currents in the plurality of coils of the coil system are adjusted by the current controller of the coil system in such a way that the magnetic forces generated by the currents and acting upon the magnetic body at multiple positions at the edge of a convex environment around the predeterminable position are directed into the environment.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
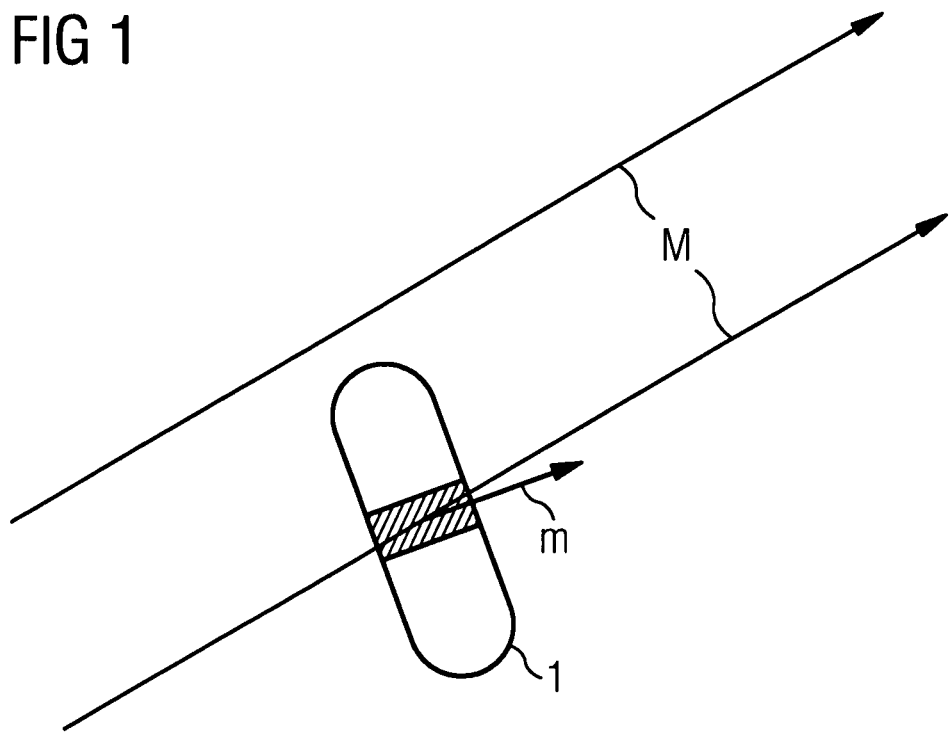
FIG. 1 shows a schematic diagram of a magnetic body in the form of a capsule for medical applications.

Reference will now be made in detail to the preferred embodiments of the present invention, examples of which are illustrated in the accompanying drawings, wherein like reference numerals refer to like elements throughout.

Proposed systems will be described below with reference to a medical device for the endoscopic examination of organs in a patient. The medical device comprises a coil system which is analogously constructed in particular to the coil system in document WO 2006/092421 A1, which is incorporated herein by reference. This coil system comprises 14 individually controllable coils for generating corresponding magnetic fields. The individual coils are designed in such a way that the magnetic field or the field gradient of the respective coils are not concentrated on one or more spatial position(s) in the work space specified by the coils. Other coil systems may optionally be used, wherein eight coils should be used as a minimum in order to be able to control the magnetic degrees of freedom independently of one another. Despite the same construction as the coil system in document WO 2006/092421 A1 the coil system used in the embodiment described hereinafter differs in the control of the currents of the individual coils.

In the embodiment described here a magnetic capsule 1 is moved by the coil system, and this is schematically reproduced in FIG. 1. The capsule is an endoscopic probe which is swallowed by the patient in order to perform corresponding examinations in the patient's gastro-intestinal tract. The capsule is a magnetic body having a magnetic dipole moment m. When a magnetic field is applied, which is schematically indicated in FIG. 1 by the field lines M, a torque is generated on the capsule 1 which aligns the magnetic dipole moment of the capsule in the direction of the magnetic field.

The capsule 1 contains a camera (not shown) and is swallowed by the patient before the endoscopic examination. The patient is positioned in the work space of the coil system in the process or thereafter. The capsule can then be moved in the coil system by appropriate adjustment of the currents, and in particular can also be aligned in a desired direction of orientation. Gastroenterological examinations by way of example can be carried out using the capsule. The patient drinks a sufficient quantity of water before and optionally also during the examination, so during the examination the capsule is moved in the water or on the surface of the water. By suitably adjusting the currents in the coils the capsule can then be moved and oriented on the surface of the water to the regions of the stomach to be examined, and close-up views, in which the capsule is completely located in the water below the surface thereof, are also possible. The capsule has a high-frequency transmitter with which the recorded images are emitted and are received outside the patient by a corresponding receiver. This receiver is, for example, integrated in a belt which the patient wears during the examination.

In the embodiment described below the movement of the capsule in a space with five degrees of freedom comprising two translational and all three rotational degrees of freedom is considered. This corresponds, for example, to the above-described movement of the capsule on the surface of the water in a patient's stomach with three rotational and only two translational degrees of freedom. The aim of the control of the currents in the coils described below is accordingly to adjust the currents in the work space of the coil system in such a way that the coils generate a magnetic field maximum at a predetermined spatial position, so the capsule moves toward this spatial position and remains there. The spatial position can be suitably adjusted and changed by an operator, i.e. the medical staff, by way of a user interface in order to perform corresponding examinations of the relevant organs in the patient.

The three-dimensional magnetic dipole moment vector of the capsule 1 will be designated $\vec{m}$ hereinafter and a coil system with $n_{coils}$ coils will be considered. The magnetic dipole moment of the capsule is generated inside the capsule by a suitable magnetic element. The specific three-dimensional spatial position, to which the capsule should move, is designated P, moreover. The magnetic field generated by the current flow in the coils is represented by the three-dimensional magnetic field vector $\vec{B}(P)$. The force generated by the magnetic field as a function of the magnetic dipole moment of the capsule and the spatial position P is reproduced by the three-dimensional force vector $\vec{F}(P, \vec{m})$. The currents in the individual coils are represented by a vector I with $n_{coils}$ entries, with each entry reflecting the current flow in a single coil. The following relationship exists between the current vector I and the magnetic field generated therefrom and the force generated therefrom at spatial position P:

$$\begin{bmatrix} \vec{B} \\ \vec{F} \end{bmatrix} = A(P, \vec{m})I$$

Here $A(P, \vec{m})$ is a $6 \times n_{coils}$ matrix. The matrix $A(P, \vec{m})$ is the product of two matrices $U(\vec{m})$ and $V(P)$, i.e. the following applies:

$$A(P,\vec{m}) = U(\vec{m})V(P)$$

The matrix V(P) is a $8 \times n_{coils}$ matrix which depends on the geometry of the coil system in addition to the specific spatial position P. The matrix is specified or can be determined without problems for any spatial position from the specific geometry of the coil system according to the biot-savart law. The additional matrix $U(\vec{m})$ is a $6 \times 8$ matrix which reads as follows:

$$U(\vec{m}) = \begin{bmatrix} 1 & 0 & 0 & 0 & 0 & 0 & 0 & 0 \\ 0 & 1 & 0 & 0 & 0 & 0 & 0 & 0 \\ 0 & 0 & 1 & 0 & 0 & 0 & 0 & 0 \\ 0 & 0 & 0 & m_x & m_y & m_z & 0 & 0 \\ 0 & 0 & 0 & 0 & m_x & 0 & m_z & m_y \\ 0 & 0 & 0 & -m_z & 0 & m_x & m_y & -m_z \end{bmatrix}$$

Here $m_x$, $m_y$, $m_z$ represent the x, y and z components of the magnetic dipole moment vector $\vec{m}$.

To calculate the matrix $U(\vec{m})$ the magnetic dipole moment $\vec{m}$, i.e. the orientation of the capsule, has to be known. As already stated, a scenario is being considered in which the capsule can move in space with five degrees of freedom, comprising all three rotational degrees of freedom. The consequence of this is that the magnetic dipole moment of the capsule is substantially (i.e. with negligible errors) aligned in the direction of the magnetic field $\vec{B}$ of the coil system acting on the capsule. To ensure this it is specified as a boundary condition hereinafter that the value of the magnetic field is greater than a minimal value, i.e. the following applies:

$$\|\vec{B}\| \geq B_{min}$$

Here $B_{min}$ is a suitably chosen scalar value which is chosen to be so large that the largest possible disturbing torque that can act on the capsule, divided by the product of $B_{min}$ and the value of $\vec{m}$ is less than the sine of the maximal admissible solid angle between $\vec{B}$ and $\vec{m}$.

The magnetic dipole moment $\vec{m}$ of the capsule is known. Therefore the relationship between the magnetic field and/or the exerted force and the current vector on the specific spatial position P can be described as follows:

$$\begin{bmatrix} \vec{B} \\ \vec{F} \end{bmatrix} = A(P)I$$

Figure 2:
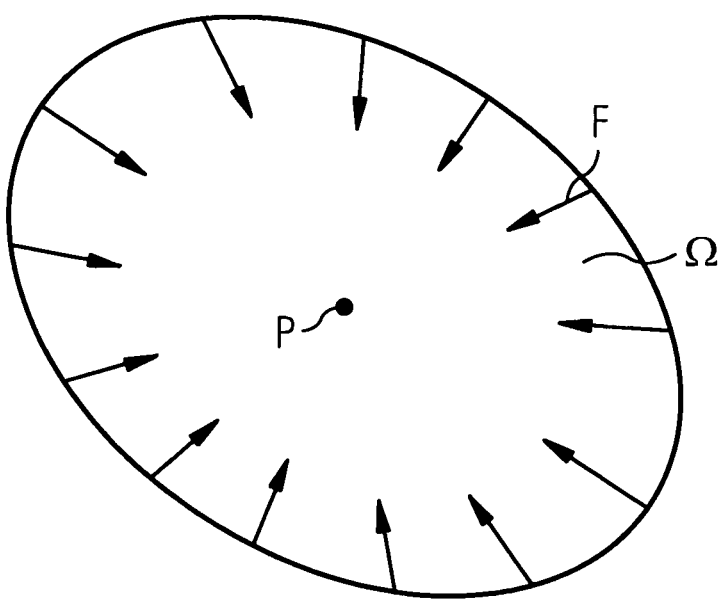
FIG. 2 shows a schematic diagram of the configuration of the magnetic forces for the movement of a capsule to a spatial position according to an embodiment of the inventors' proposals.

As already stated, the currents in the coil system should accordingly be adjusted in such a way that a magnetic field with a maximum is generated at point P. This occurs by way of the solution of a convex optimization problem, taking account of the boundary condition that the magnetic forces align in relation to the specific spatial position, as indicated in FIG. 2. FIG. 2 shows the specific spatial position P and a predetermined environment Ω around the spatial position. For reasons of clarity a two-dimensional environment is reproduced. The optimization can, however, optionally also be applied to three-dimensional environments. The alignment of the forces on the closed edge of this environment is indicated by a large number of arrows, one of the arrows, by way of example, being designated F. The alignment of the forces at the corresponding positions at the edge of the environment (which tally with the respective origins of the arrows) must be such that every force that is exerted on the magnetic body at the respective edge position is directed into the environment Ω. This criterion is taken into account in the optimization problem described below as a necessary boundary condition.

The optimization problems formulated below are convex optimization problems which can be reliably and efficiently solved using convex optimization methods that are sufficiently known from the related art. In the scenario described here of the magnetic navigation of a magnetic capsule the optimization problem can also be solved in real time. In other words, the current controller of the coil system contains a computing unit which solves a corresponding optimization problem, independently of the selected orientation and position to which the capsule should move, and adjusts the current values that result therefrom. It is optionally also possible to determine in advance for a large number of orientations and positions in the work space of the coil space the currents that are to be adjusted accordingly and to store them in a memory in the current controller of the coil system.

The optimization problem to be solved will be described hereinafter on the basis of a movement of the capsule in which no forces act on the capsule in the y direction and the capsule cannot experience a translational movement in the y direction either. This corresponds to the above movement with two translational degrees of freedom, wherein only one translational movement of the capsule is possible in the x and z directions. In addition the capsule can rotate as desired, i.e. all three possible degrees of freedom exist for rotation.

The relationship between the current vector and the magnetic field and the exerted magnetic force can be written as follows:

$$B_x(P)=A_1(P)I$$
$$B_y(P)=A_2(P)I$$
$$B_z(P)=A_3(P)I$$
$$F_x(P)=A_4(P)I$$
$$F_y(P)=A_5(P)I$$
$$F_z(P)=A_6(P)I$$

Here $A_i$ designates the rows i of the above matrix $A(P)$.

The desired orientation $\vec{m}_{desired}$ of the magnetic dipole and therefore the desired orientation of the magnetic field is suitably fixedly chosen in advance and is arbitrary in the exemplary embodiment described here. There is always the possibility of (x, y, z) coordinate systems being aligned in such a way that the vector $\vec{m}_{desired}$ is aligned in the x axis of the coordinate system. The scenario will therefore be considered hereinafter, without limiting the generality, that only the x component $B_x$ of the magnetic field is given as not being equal to zero, whereas the y component $B_y$ and the z component $B_z$ are substantially zero.

Two vectors $\vec{T}_x=[d_{peak\ width}, 0, 0]^T$ and $\vec{T}_z=[0, 0, d_{peak\ width}]^T$ will be considered hereinafter, where $d_{peak\ width}$ is a positive scalar distance value, typically in a range between 0.01 and 0.1 m. Four points $P_1, P_2, P_3, P_4$ in the working volume of the coil systems are defined by the above vectors $\vec{T}_x$ and $\vec{T}_z$ as follows:

$$P_1=P-\vec{T}_z$$
$$P_2=P+\vec{T}_x$$
$$P_3=P+\vec{T}_z$$
$$P_4=P-\vec{T}_x$$

Figure 3:
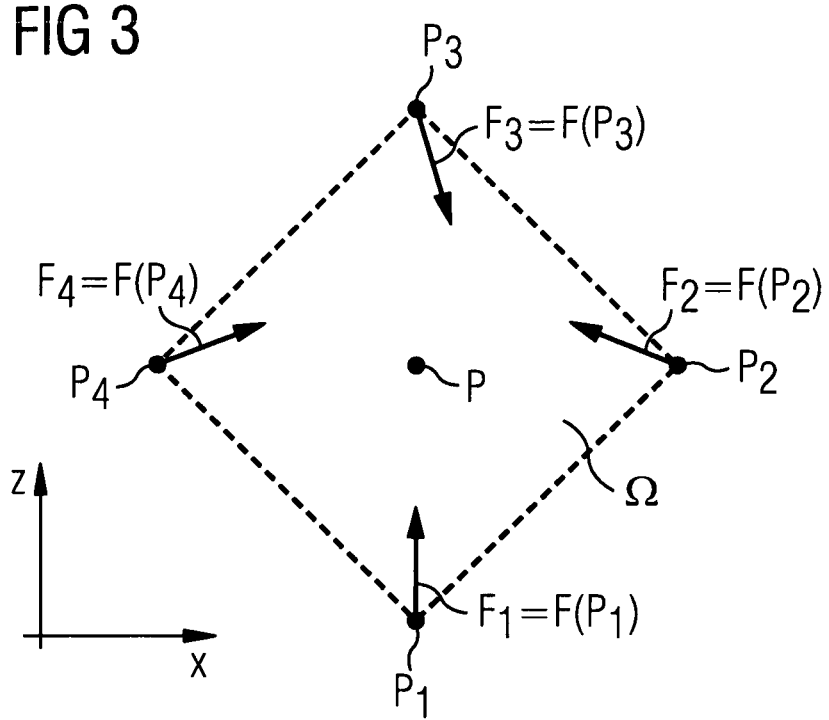
FIG. 3 shows a schematic diagram of the optimization problem of the invention for the movement of a capsule with two translational degrees of freedom.

These points are illustrated by way of example in FIG. 3. FIG. 3 shows in the x-z plane the specific point P toward which the capsule should move. A corresponding environment Ω is given for this point P, where the edge of the environment is a rectangle, which is reproduced in FIG. 3 in broken lines. The corresponding points $P_1$ to $P_4$ are located at a spacing $\vec{T}_x$ shifted to the left or right of or at a spacing shifted above or below point P. The forces $F_1=F(P_1)$ at point $P_1$, $F_2=F(P_2)$ at point $P_2$, $F_3=F(P^3)$ at point $P_3$ and $F_4=F(P_4)$ at point $P_4$ generated by the magnetic field of the coils system are considered in the subsequent optimization, with the points always having to be directed into the environment Ω.

Overall the following boundary conditions relating to the generation of a magnetic field maximum must be given in the environment of the specific spatial point P:

1. The magnetic field $\vec{B}$ at the specific position P must be strong enough and correctly aligned so the desired orientation of the capsule is achieved. The magnetic field $\vec{B}$ must therefore have roughly the same direction in a sufficiently large environment around point P. This environment should contain at least the above positions $P_1, P_2, P_3, P_4$. This condition is fulfilled if a sufficiently strong magnetic field is demanded at the specific spatial position P.

2. For the points $P_1, P_2, P_3, P_4$ on a predetermined convex environment, which according to FIG. 3 is represented by a rectangle, the magnetic force lies on the capsule in each of these points within this convex environment, i.e. the magnetic force is directed into the convex environment. In the case where there are no external disruptions, it is therefore ensured that, following entry into the convex environment, the capsule will never leave this environment as the forces are always directed such that the capsule is pushed into the environment. It is also ensured that the point at which the magnetic force disappears lies within this convex environment in the vicinity of point P. Consequently, in the absence of external disruptions, the capsule will always move toward the specific point P and also remain there.

3. The absolute value of the currents in the individual coils must be less than respective maximal values. Without limiting the generality it is assumed in the exemplary embodiment described here that the maximum current is equal for each coil. This current is designated $I_{max}$ hereinafter.

The above conditions 1, 2 and 3 can be described as a convex optimization problem. In one variant the optimization is described as a maximization of the respective currents in the individual coils. For a predetermined maximal current $I_{max}$, a minimal magnetic field $B_{min}$, in the x direction and a predetermined constant c (which should be small and is typically less than 0.01), according to the optimization problem values I, ϵ, δ are sought, so the following applies:

$$\max_{I,\delta,\epsilon}\epsilon$$

$$\epsilon>0, \delta>0, \delta<\epsilon$$

$$B_x(P)>B_{min}$$

$$B_y(P)<cB_{min}$$

$$B_z(P)<cB_{min}$$

$$F_z(P_1)>\epsilon$$

$$-\delta<F_x(P_1)<\delta$$

$$F_z(P_3)<-\epsilon$$

$-\delta<F_x(P_3)<\delta$ $-\delta<F_z(P_2)<\delta$ $F_x(P_2)<-\epsilon$ $-\delta<F_z(P_4)<\delta$ $F_x(P_4)>\epsilon$ $I_{max}<I<I_{max}$, komponentenweise$_{component-wise}$ Here the variables $\epsilon$ and $\delta$ represent force values which according to the above optimization should be selected in such a way that the force which pushes the capsule into the center of the rectangle with the corners $P_1$ to $P_4$, is maximized, wherein corresponding restrictions in relation to the magnetic field, the force direction and the currents should be heeded as boundary conditions. The boundary condition $0<\delta<\epsilon$ together with the boundary conditions in relation to the components of the corresponding forces $F_1$ to $F_4$ at the points $P_1$ to $P_4$ ensure that the magnetic forces always point into the rectangle formed by the points $P_1$ to $P_4$.

The above optimization problem is a linear program as the forces and fields are linear combinations of the currents. The solution to such optimization problems is sufficiently known from the related art and any standard method may be used to solve this problem.

In a second variant the optimization problem is formulated in such a way that a minimal value of the above force value $\epsilon$ is specified and the Euclidean norm of the currents is minimized. In this case variables I, $\delta$ are sought for predetermined variables $\epsilon$, $B_{min}$, and c, so the following applies:

$\min_{\delta,I}\|I\|^2$ $\delta>0, \delta<\epsilon$ $B_x(P)>B_{min}$ $B_y(P)<cB_{min}$ $B_z(P)<cB_{min}$ $F_z(P_1)>\epsilon$ $-\delta<F_x(P_1)<\delta$ $F_z(P_3)<-\epsilon$ $-\delta<F_x(P_3)<\delta$ $-\delta<F_z(P_2)<\delta$ $F_x(P_2)<-\epsilon$ $-\delta<F_z(P_4)<\delta$ $F_x(P_4)>\epsilon$ The boundary condition $-I_{max}<I<I_{max}$ can optionally also be taken into account in this optimization problem.

In contrast to the preceding optimization problem this optimization problem is a quadratic program with linear side conditions. The solution to such optimization problems is also sufficiently known from the related art and a standard method may be used for the solution. The above optimization problems can also be simply expanded by taking into account different weights for the currents, so, for example, the resistance losses in the coil system are minimized.

Figure 4:
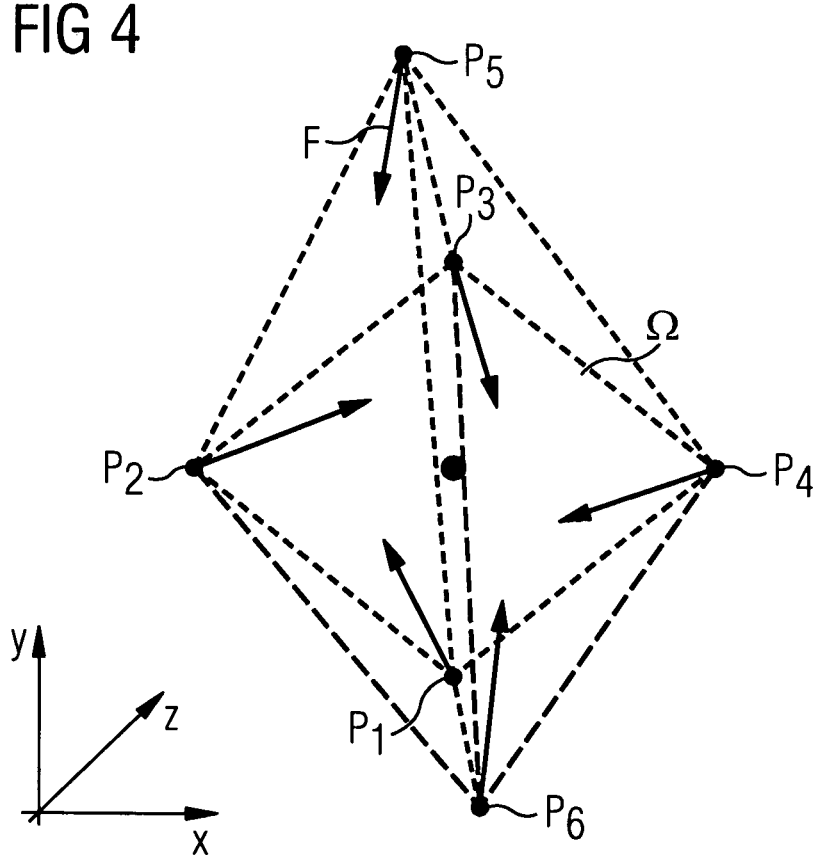
FIG. 4 shows a schematic diagram of the optimization problem for the movement of a capsule with three translational degrees of freedom.

The embodiments described above have been described using the example of a movement of the capsule with two translational and three rotational degrees of freedom. The proposed systems may optionally also be used for the movement of a capsule with more or less translational or rotational degrees of freedom. By way of example a scenario is shown in FIG. 4 in which the translational degree of freedom of a movement also exists in the y direction. Instead of a rectangle according to FIG. 3, the environment Ω is described by a polyhedron which has six corners $P_1$ to $P_6$. Analogous to the embodiment in FIG. 3 the boundary condition that the magnetic forces in the individual points $P_1$ to $P_6$ are directed into the polyhedron should also be taken into account in the solution to the optimization problem. By way of example corresponding magnetic forces are again indicated by arrows, wherein for reasons of clarity only one of the arrows is designated by reference character F.

The variants of the method just described have a series of advantages. In particular the mechanical movement of a patient or the coil system during the medical examination of the patient is no longer required. Furthermore, it is no longer necessary for the position of the capsule in the work space of the coil system to be measured because by appropriate adjustment of the currents independently of its current position the capsule always moves toward the position of the magnetic field maximum.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004).

The invention claimed is:

1. A coil system for contactless magnetic navigation of a magnetic body in a work space, comprising:
   a plurality of coils; and
   a current controller for controlling respective currents in the plurality of coils to navigate the magnetic body to a variably predeterminable position in the work space, the current controller controlling the currents in the plurality of coils in such a way that magnetic forces are generated by the currents at multiple locations on an edge of an enclosed environment around the predeterminable position, each of the magnetic forces being directed from the edge into an area of the enclosed environment to generate a magnetic field maximum at the predeterminable position, the magnetic field maximum moving the magnetic body to, or holding the magnetic body at, the predeterminable position.

2. The coil system as claimed in claim 1, wherein the magnetic body is navigated without information on a current position or a current orientation of the magnetic body.

3. The coil system as claimed in claim 1, wherein the environment is designed in such a way that a maximum spacing of the edge of the environment to the predeterminable position is between 0.005 and 0.1 meters.

4. The coil system as claimed in claim 1, wherein the environment around the predeterminable position is a polygon.

5. The coil system as claimed in claim 4, wherein the multiple locations are corners of the polygon.

6. The coil system as claimed in claim 1, wherein the environment around the predeterminable position is a polyhedron.

7. The coil system as claimed in claim 6, wherein the multiple locations are corners of the polyhedron.

8. The coil system as claimed in claim 1, wherein the current controller calculates the currents to achieve the predeterminable position during operation of the coil system.

9. The coil system as claimed in claim 1, wherein a plurality of current combinations to achieve a plurality of predeterminable positions are stored in a memory of the current controller.

10. The coil system as claimed in claim 1, wherein the currents required to navigate the magnetic body to the predeterminable position represent a solution to an optimization problem with a boundary condition that the magnetic forces are directed into the environment.

11. The coil system as claimed in claim 10, wherein the optimization problem is a linear problem.

12. The coil system as claimed in claim 10, wherein the optimization problem is a quadratic problem.

13. The coil system as claimed in claim 10, wherein
the optimization problem is a minimization of a current vector comprising the currents in the plurality of coils,
an additional boundary condition on the optimization problem is that the magnetic forces generated by the currents each exceed a respective predetermined value.

14. The coil system as claimed in claim 10, wherein
the optimization problem is a maximization of the magnetic forces generated by the currents, and
an additional boundary condition on the optimization problem is that the currents in the plurality of coils each are below a respective maximum value.

15. The coil system as claimed in claim 10, wherein an additional boundary condition on the optimization problem is that the magnetic field maximum at the predeterminable position is substantially directed in a predetermined direction and has a value which exceeds a predetermined value.

16. The coil system as claimed in claim 10, wherein, when solving the optimization problem, the respective currents of the plurality of coils are weighted differently.

17. The coil system as claimed in claim 1, wherein the current controller controls movement of the magnetic body with two translational degrees of freedom or less.

18. A medical device for contactless magnetic navigation of a magnetic probe inside a patient's body, comprising:

a plurality of coils surrounding a work space in which the patient is positioned; and a current controller for controlling respective currents in the plurality of coils to navigate the magnetic probe to a variably predeterminable position in the patient's body, the current controller controlling the currents in the plurality of coils in such a way that magnetic forces are generated by the currents at multiple locations on an edge of an enclosed environment around the predeterminable position, each of the magnetic forces being directed from the edge into an area of the enclosed environment to generate a magnetic field maximum at the predeterminable position, the magnetic field maximum moving the magnetic probe to, or holding the magnetic probe at, the predeterminable position.

19. The medical device as claimed in claim 18, wherein the magnetic body is navigated without moving the coil system with respect to the patient.

20. A method for the contactless magnetic navigation of a magnetic body in a work space, comprising:

providing a plurality of coils around the work space; and controlling respective currents in the plurality of coils to navigate the magnetic body to a variably predeterminable position in the work space, the currents in the plurality of coils being controlled in such a way that magnetic forces are generated by the currents at multiple locations on an edge of an enclosed environment around the predeterminable position, each of the magnetic forces being directed from the edge into an area of the enclosed environment to generate a magnetic field maximum at the predeterminable position, the magnetic field maximum moving the magnetic body to, or holding the magnetic body at, the predeterminable position.

* * * * *